United States Patent [19]

Jendrisak et al.

[11] Patent Number: 4,766,072
[45] Date of Patent: Aug. 23, 1988

[54] VECTORS FOR IN VITRO PRODUCTION OF RNA COPIES OF EITHER STRAND OF A CLONED DNA SEQUENCE

[75] Inventors: Jerome J. Jendrisak; Martin K. Lewis, both of Madison; Michael J. Fiandt, Cambridge, all of Wis.

[73] Assignee: Promega Corporation, Madison, Wis.

[21] Appl. No.: 756,053

[22] Filed: Jul. 17, 1985

[51] Int. Cl.$^4$ ............... C12P 19/34; C12N 15/00; C12N 7/00
[52] U.S. Cl. ................ 435/91; 435/172.3; 435/235; 435/320; 935/3; 935/16; 935/17; 935/29; 935/41
[58] Field of Search ............ 435/91, 172.3, 235, 435/320; 536/27; 935/34, 29, 41, 16, 17, 31

[56] References Cited

U.S. PATENT DOCUMENTS

| | | | |
|---|---|---|---|
| 4,237,224 | 12/1980 | Cohen et al. | 435/68 |
| 4,349,629 | 9/1982 | Carey et al. | 435/172.3 |
| 4,394,443 | 7/1983 | Weissman et al. | 435/6 |
| 4,403,036 | 9/1983 | Hartley et al. | 435/68 X |
| 4,495,280 | 1/1985 | Bujard et al. | 435/6 |
| 4,528,266 | 7/1985 | Pieczenik | 435/6 |
| 4,551,433 | 11/1985 | DeBoer | 435/253 |

OTHER PUBLICATIONS

Axelrod, V. D. et al., *Biochemistry*, vol. 24, 5716–5723, Oct., 1985.
Schmeisser, V. et al. *Proc. Natl. Acad. Sci.*, vol. 77, No. 6, pp. 3191–3195, 1980.
Gussin, G. et al., in *Lambda II*, Cold Spring Harbor Laboratory, (Eds. R. Hendrix et al.), pp. 108–110, 1983.
Dunn, J. et al., *J. Molec. Biology*, vol. 166, pp. 477–535, 1983.
McAllister, W. et al., *J. Mol. Biol.*, vol. 153, pp. 527–544, 1981.
"Riboprobe Gene Analysis System", brochure published by Promega Corporation, Copyright 1984.
Hakan Persson, et al., "Antibodies to Human c-myc Oncogene Product: Evidence of an Evolutionarily Conserved Protein Induced During Cell Proliferation", Aug. 17, 1984.
Eugene T. Butler, et al., "Bacteriophage SP6-Specific RNA Polymerase", *The Journal of Biological Chemistry*, vol. 257, No. 10, Issue of May 25, 1982, pp. 5772–5778.
Kathleen H. Cox, et al., "Detection of mRNAs in Sea Urchin Embryos by In Situ Hybridization Using Asymmetric RNA Probes", Developmental Biology 101 (1984), pp. 485–502.
Adrian R. Krainer, et al., "Normal and Mutant Human B-Globin Pre-mRNAs are Faithfully and Efficiently Spliced In Vitro", Cell, vol. 36, Apr., 1984, pp. 933–1005.

(List continued on next page.)

Primary Examiner—Thomas G. Wiseman
Assistant Examiner—Jayme A. Huleatt
Attorney, Agent, or Firm—Isaksen, Lathrop, Esch, Hart & Clark

[57] ABSTRACT

In vitro production of RNA copies of either strand of any cloned DNA sequence may be obtained utilizing a unique cloning vector having two different opposed promoter sequences which are separated by a multiple cloning site. RNA polymerases which recognize only one of the particular promoter sequences in the vector may be applied to obtain transcription which proceeds from the recognized promoter toward the other promoter. Transcription of a desired strand of any DNA sequence is obtained by cleaving a particular restriction site in the multiple cloning site between the two promoter sequences, cloning the desired DNA sequence into the cleaved site, then cleaving another site between the two promoters which is distal to the promoter from which transcription is desired. The RNA polymerase which recognizes the selected promoter may then be applied to the vector to obtain transcription of the selected DNA sequence in vitro. Double stranded RNA may also be formed utilizing the vector by providing multiple vectors cleaved on either side of the DNA segment and thereafter applying the two RNA polymerases to cause transcription of both strands of the selected DNA segment. Specific cloning vectors are novel plasmids designated pGEM-1 and pGEM-2 which are characterized by having the SP6 and T7 late phage promoters facing each other separated by a multiple cloning site.

20 Claims, 6 Drawing Sheets

OTHER PUBLICATIONS

John J. Toole, et al., "Molecular Cloning of a cDNA Encoding Human Antihaemophilic Factor", Nature, vol. 312 22, Nov. 1984, pp. 342–347.

Thomas A. Kunkel, et al., "Single-Stranded Binding Protein Enhances Fidelity of DNA Synthesis In Vitro", Proc. Natl. Acad. Sci. USA, vol. 76, No. 12, pp. 6331–6335, Dec. (1979).

P. A. Krieg, et al., "Functional Messenger RNAs are Produced by SP6 In Vitro Transcription of Cloned cDNAs", Nucleic Acids Research, vol. 12, No. 18 (1984), pp. 7057–7070.

D. A. Melton, et al., "Efficient In Vitro Synthesis of Biologically Active RNA and RNA Hybridization Probes from Plasmids Containing a Bacteriophage SP6 Promoter", Nucleic Acids Research, vol. 12, No. 18 (1984), pp. 7035–7056.

Stanley Tabor, et al., "A Bacteriophage T7 RNA Polymerase/Promoter System for Controlled Exclusive Expression of Specific Genes", Proc. Natl. Acad. Sci. U.S.A., vol. 82, Feb. 1985, pp. 1074–1078.

→ SP6 TRANSCRIPTION START

ATTTA    GGTGA    CACTA    TAGAA    TACAA    GCTTG
                                    └─────────┘
                                      Hind III GGCTG    CAGGT    CGACT    CTAGA
└────┬───┘────────┘───┬────┘
   Pst I    Sal I    Xba I
            Acc I
            Hinc II GGATC    CCCGG    GCGAG    CTCGA    ATTCG
└──┬──┘──┘──┬──┘──┘──┬──┘──┘──┬──┘
 Bam HI   Sma I    Sac I    Eco RI
          Ava I

GATCG    ATCCG    ATCCC    GCTAG    AGGGA    AACCG

TTGTG    GTCTC    CCTAT    AGTGA    GTCGT    ATTA
T7 TRANSCRIPTION START ←┘

FIG. 8

VECTORS FOR IN VITRO PRODUCTION OF RNA COPIES OF EITHER STRAND OF A CLONED DNA SEQUENCE

FIELD OF THE INVENTION

This invention pertains generally to the field of molecular biology and particularly to the production of RNA in vitro.

BACKGROUND OF THE INVENTION

Through the development of recombinant DNA techniques, it has become fairly straightforward to clone DNA sequences from essentially any organism into plasmid or viral vectors for propagation and amplification in a foreign host. In this form the DNA can be studied with regard to its sequence, structure, coding capacity, or other properties. It can also be used for a variety of applications such as detection of complementary sequences in samples, generation of altered forms of a gene product, modulation of organismal function through insertion into new organisms, etc. Some vectors contain DNA sequences near the insertion site for foreign DNA which control the expression of the inserted DNA in the host cell. These vectors can be used to produce the product of a cloned gene in a host such as *Escherichia coli*.

More recently it has become possible to efficiently control the expression of cloned DNA sequences in vitro. The first system to be widely exploited for this purpose used a plasmid containing a late promoter from the *Salmonella typhymurium* bacteriophage SP6 and a purified DNA dependent RNA polymerase purified from the virus infected cells. Krieg, P. A. and Melton, D. A. (1984) Nucleic Acids Res. 12:7057-7070; Butler, E. T. and Chamberlin, M. J. (1982) J. Biol. Chem. 257:5772-5778. Using this system, an RNA copy of one strand of any DNA sequence inserted into the vector can be produced. The vector is constructed such that several unique restriction enzyme sites lie adjacent to the SP6 promoter to allow the insertion of a variety of DNA sequences into that region. The plasmid is then propagated in and purified from *E. coli*. Next, the purified plasmid is converted to a linear piece of DNA through the action of a restriction enzyme that cuts next to the inserted DNA on the side distal to the promoter. The purified RNA polymerase is added to the linearized DNA along with a substrate mixture and large amounts of the desired RNA can be produced. This RNA can be used as a hybridization probe, as a substrate for RNA processing enzymes, or as mRNA for synthesizing protein by in vitro translation. The relatively large amounts of RNA so produced are readily studied from a variety of structural and functional perspectives.

An analogous system has been configured using a different promoter and RNA polymerase from the *E. coli* bacteriophage T7. The T7 enzyme recognizes a specific DNA promoter sequence and has similar properties to the SP6 derived enzyme. Both the SP6 and T7 enzymes are extremely specific as they only recognize their own late phage promoters for in vitro transcription. The transcription reactions for either promoter system are very efficient and many copies of full length RNA may be produced from each template molecule. It is thus possible to synthesize milligram amounts of RNA from any cloned DNA sequence.

The above described in vitro transcription systems have the disadvantage that only one strand of the DNA molecule can be copied into RNA. For many applications an RNA copy of a specific strand of the DNA is needed, as for in vitro translation or RNA processing or synthesizing probes for RNA detection. At the time the DNA sequence is cloned into the vector, it often is not known which strand will be required and it often is not possible to control the orientation of the insertion. In such cases, the DNA must be inserted into two different vectors or a number of isolates must be generated and examined to obtain two plasmids which carry the same DNA sequence in opposite orientations with respect to the promoter. For other applications, such as processing double-stranded RNA, both strands of the DNA must be copied into RNA, again requiring much more effort since plasmids with the DNA in two orientations must be isolated.

SUMMARY OF THE INVENTION

In accordance with the present invention, it is possible to obtain RNA copies of one or both strands of a chosen DNA sequence which is inserted in a single cloning vector, for example, a plasmid. Since only one vector is required, the efficiency of the production of the desired RNA is significantly improved.

The vector utilized in the invention has two different promoter sequences separated by a series of unique restriction sites into which foreign DNA can be inserted. The promoters face each other such that transcription from either promoter proceeds toward the other. Each promoter sequence is associated with a unique RNA polymerase which recognizes only that promoter sequence in the vector. The cloning site which separates the promoters has at least one and preferably several distinct cleavage sites cleaved by distinct restriction enzymes which recognize no other sites in the vector.

Preferred plasmid vectors constructed in accordance with the invention, designated pGEM-1 and pGEM-2, are derived from suitably transformed isolates of plasmids from *E. coli*. The promoters contained in the vectors pGEM-1 and pGEM-2 originate from two bacteriophage, the *Salmonella typhymurium* virus SP6 and the *E. coli* virus T7. Each RNA polymerase for these two promoters is highly active in vitro and is specific to its own promoter. No known DNA sequences other than those from the respective viruses which are used as the promoters are recognized by these enzymes, providing extreme specificity to the RNA transcripts which are produced. The opposed promoters in the plasmids pGEM-1 and pGEM-2 are separated by a multiple cloning site containing eleven restriction sites which are unique within the vectors. The vectors pGEM-1 and pGEM-2 differ only in the orientation of the restriction sites in the multiple cloning site with respect to the two opposed promoter sequences.

The vector is utilized by applying a restriction enzyme specific to a selected restriction site in the multiple cloning site to cleave the vector at that site. A selected DNA sequence is then cloned into the vector and another restriction enzyme is applied to the vector which is specific to a restriction site between the inserted DNA and one of the promoters to cleave the vector at that site. If the orientation of the insert DNA is known, it can be cloned in a particular orientation by cleaving the vector and the insert DNA with two restriction enzymes that recognize unique sites in the multiple cloning site. An RNA polymerase specific to the promoter sequence remaining adjacent to the inserted DNA is then applied in a suitable RNA generating medium to generate mRNA copies of the DNA segment. The particular strand of the DNA segment which is transcribed is selected by cleaving on the side of the DNA segment away from the promoter from which the transcription is desired to take place followed by transcription using the appropriate RNA polymerase.

Double stranded RNA can also be readily produced by separating the vectors into two groups and cleaving one group with an endonuclease specific to a site between the DNA segment at one of the promoters and cleaving the second group with an endonuclease specific to a site between the DNA segment and the second promoter. The cleaved vectors may then be used to produce complementary RNA strands which can be hybridized to form double stranded RNA.

Further objects, features, and advantages of the invention will be apparent from the following detailed description of the invention and the illustrative drawings.

BRIEF DESCRIPTION OF THE DRAWINGS

In the drawings:

FIG. 8 is the promoter and multiple cloning site sequence for the plasmid pGEM-0 showing the coding strand for T7 RNA polymerase and the non-coding strand for SP6 RNA polymerase.

DETAILED DESCRIPTION OF THE INVENTION

Figure 2:
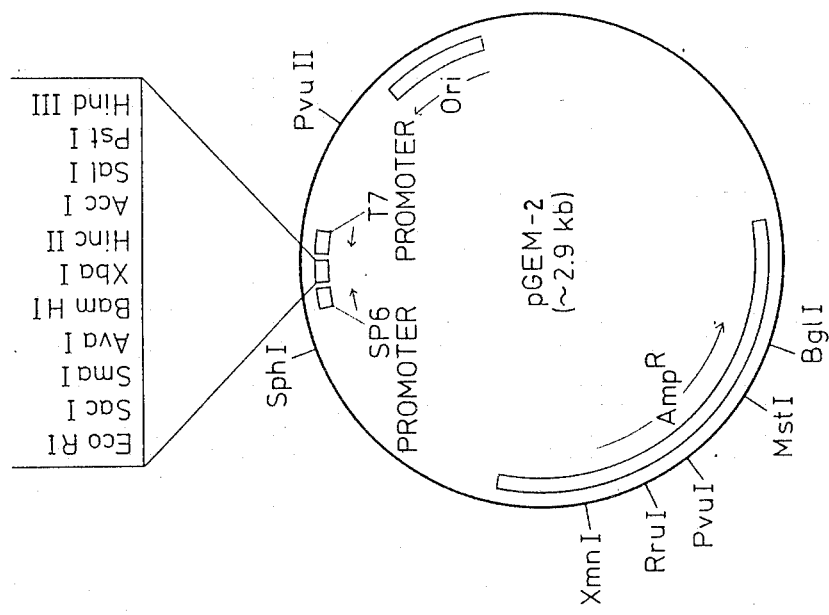
FIG. 2 is a partial restriction site and functional map of the plasmid pGEM-2.

The present invention allows selective transcription of RNA in vitro from either strand of a DNA sequence using a single vector regardless of the orientation of the DNA segment inserted in the vector. The vector constructed in accordance with the invention has two distinct promoter sequences capable of promoting transcription in vitro of a DNA segment inserted between them. The two promoters must face each other; that is, they must be oriented such that transcription from either promoter proceeds toward the other. Thus, RNA may be transcribed from either strand of the DNA segment depending upon the promoter at which the transcription begins. At least one restriction site must be present between the opposed promoters which can be cleaved to allow insertion of foreign DNA. However, as explained below, a number of additional restriction sites in the cloning site between the promoters is preferred to allow selection of a site that matches the cleaved ends of the DNA segment to be inserted. Multiple unique sites between the promoters are also preferred since, as explained further below, after insertion of the DNA segment, the vector is preferably cleaved at a position adjacent to the inserted segment and distal to the desired promoter at which transcription is to begin.

A variety of vectors can be constructed to contain a region having the two facing opposed promoters and the internal cloning site as described above. The rest of the vector can be designed as desired to have specific cloning or propagation advantages relating to a particular cloning application, and the construction of the remaining portion of the vector is not critical to the functioning of the transcription region. Vectors which may be used in conjunction with the invention include a variety of plasmids which contain genes facilitating selection, for example, genes contributing antibiotic resistance; bacteriophage vectors such as lambda or related phages; shuttle vectors designed to be propagated both in prokaryotes and eukaryotes, such as *E. coli*/yeast vectors; vectors which produce fusion proteins or which fuse the cloned DNA with regions of the vector which control expression; vectors capable of transforming mammalian cells and which might either integrate into the genome or be maintained or replicated extrachromosomally; and viral vectors for use with mammalian cells.

The two opposed promoters in the transcription segment must be capable of in vitro transcription and purified RNA polymerases which uniquely recognize only one of the two promoters are required. Two particularly suitable polymerases, both presently available commercially, are the SP6 polymerase derived from the *S. typhymurium* phage SP6, and the T7 polymerase derived from the *E. coli* phage T7. Suitable polymerases are also available for the T3 and N4 phage promoters and the ghl (Pseudomonas host) promoter. Many other polymerases and the promoters they recognize can be used in accordance with the invention. These include *E. coli* RNA polymerase with various promoters, *Bacillus subtilis* RNA polymerases with various sigma-like subunits and related promoters, other suitably specific bacteriophage polymerases and their promoters, and various plant and animal derived RNA polymerases and their promoters.

The following examples are provided as illustrative of the methods for generating vectors in accordance with the invention, the vectors generated, and the methods for in vitro production of RNA coded by the vectors.

EXAMPLE 1

Construction of plasmid pGEM-1

Figure 1:
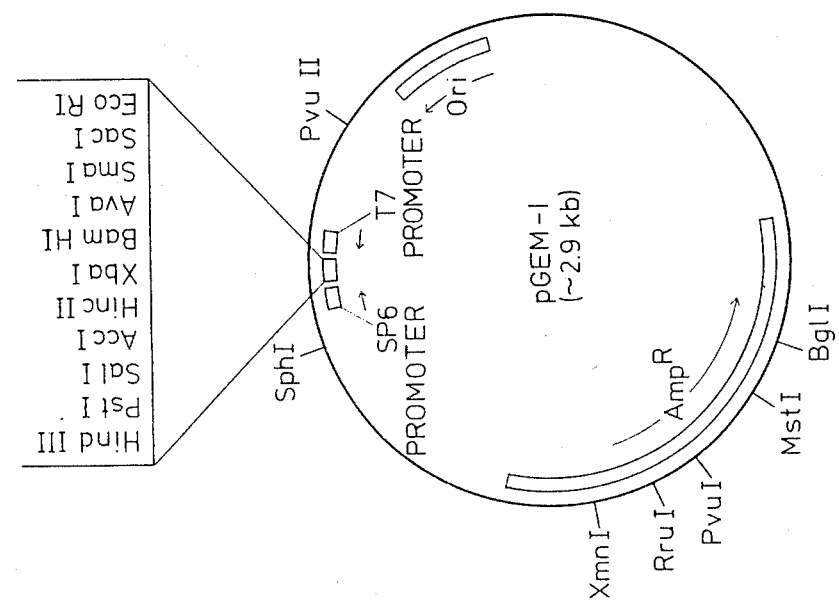
FIG. 1 is a partial restriction site and functional map of the plasmid pGEM-1.
Figure 4:
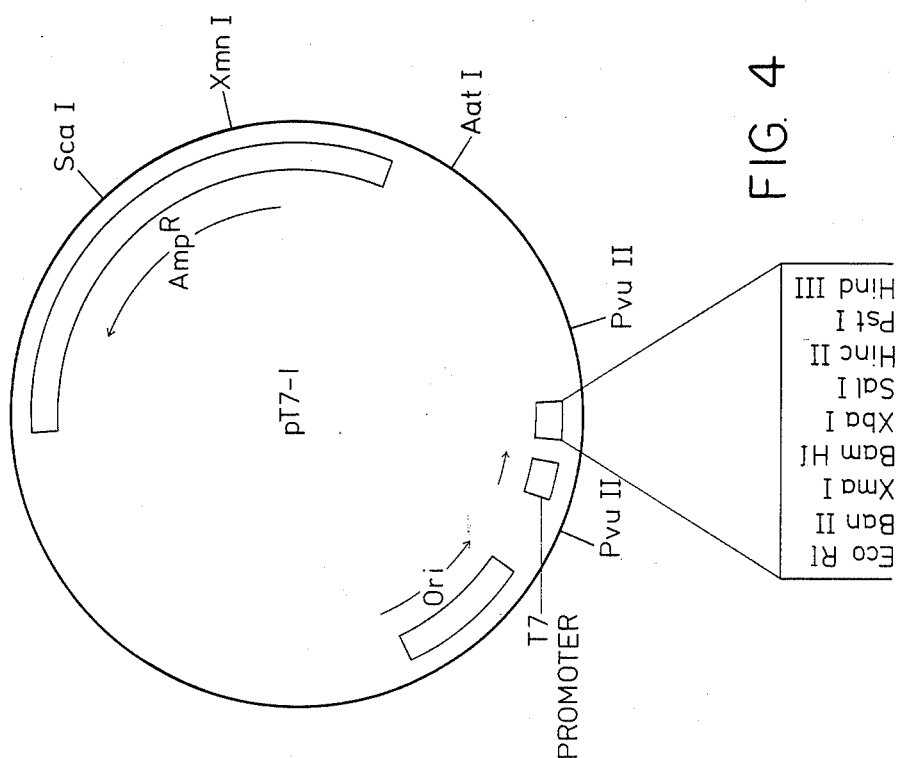
FIG. 4 is a partial restriction site and functional map of the parent plasmid pT7-1.

A plasmid designated pGEM-1 having the restriction and functional map shown in FIG. 1 was constructed from the parent plasmid pSP64 (Melton, D. A., et al. (1984) Nucleic Acids Research 12:7035-7056; Cox K. H., DeLeon D. V., Angerer L. M., and Angerer R. C. (1984) Dev. Biol. 101:485-502; Krainer A. R., Maniatis T., Ruskin B., and Green M. R. (1984) Cell 36:993-1005; Persson H., Hennighausen L., Taub R., DeGrado W., and Leder P. (1984) Science 225:687-693; Toole J. J. et al. (1984) Nature 312:342-347) and the parent plasmid pT7-1. The plasmid pT7-1 has the partial restriction and functional map shown in FIG. 4 and is available commercially from United States Biochemical Corporation, Cleveland, Ohio (Tabor, S. and Richardson, C. (1985) Proc. Nat. Acad. Sci. 82:1074–1078). The parent plasmids were codigested with the restriction enzymes Eco R1 and Pvu II. The fragments were then mixed and ligated using DNA ligase. The ligation mixture was used to transform competent *E. coli*, strain HB101. Isolates containing the ampicillin resistance gene (Amp$^R$) were selected on plates containing ampicillin. DNA was extracted from individual isolates and the size of the plasmid in each estimated on agarose gels. Isolates were selected which contained a plasmid of approximately 2.9 kilobases (kb) which is the size expected when the 0.18 kb Eco R1-Pvu II fragment of pSP64 is replaced by the 0.05 kb Eco R1-Pvu II fragment of pT7-1 which contains the T7 promoter.

Figure 6:
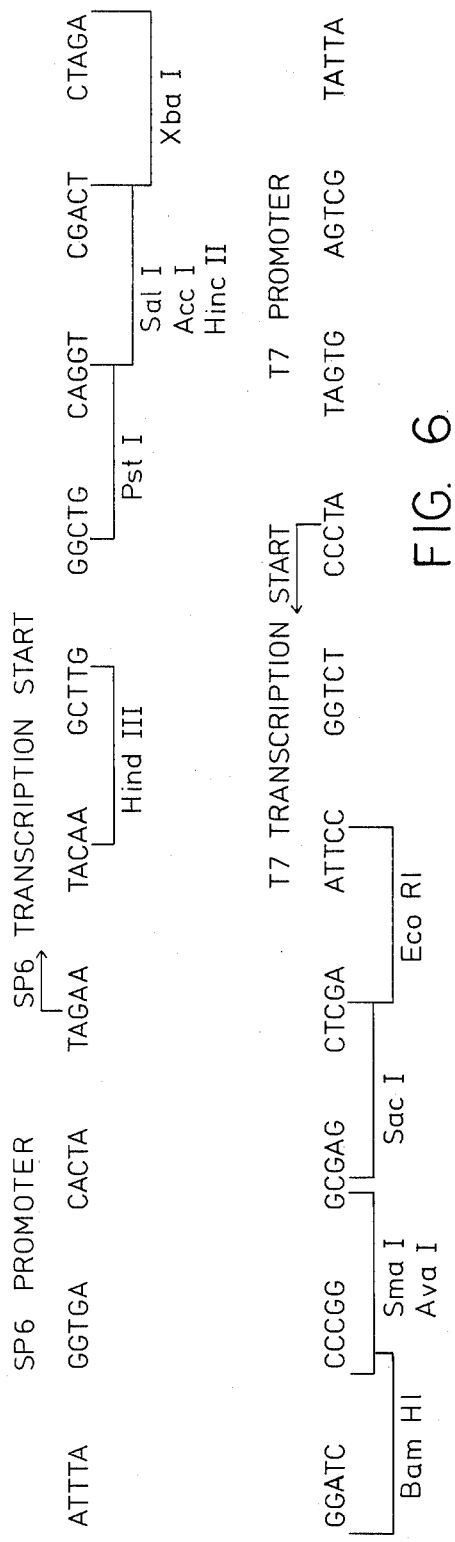
FIG. 6 is the promoter and multiple cloning site sequence for the plasmid pGEM-1 showing the coding strand for T7 RNA polymerase and the non-coding strand for SP6 RNA polymerase.

Specifically, one microgram of pT7-1 was digested with 20 units of Eco R1 restriction endonuclease (available from Promega Biotec, Madison, Wis.) and 20 units of Pvu II restriction endonuclease (Promega Biotec, Madison, Wis.) for 30 minutes at 37° C. in buffer consisting of 90 mM Tris-HCl pH 7.5, 0.1 mg/ml bovine serum albumin (BSA), 50 mM NaCl and 10 mM MgCl$_2$ in a volume of 50 microliters. One microgram of pSP64 was digested similarly. The digests were mixed together and to the resulting 0.1 ml reaction was added 0.01 ml of 10× ligase buffer (10× ligase buffer=0.1M MgCl$_2$, 0.1M DTT, 4 mM ATP, 0.3M Tris-HCl pH 7.8) and 20 Weiss units of T4 DNA ligase (Promega Biotec, Madison, Wis.). Ligation was then allowed to proceed for 2 hours at 22° C. After this time the reaction was heated for 10 minutes at 65° C. 0.02 ml of the reaction was then used to transform 0.2 ml of competent *E. coli* HB101. Competent cells were prepared according to Maniatis T., Fritsch E. F., and Sambrook J. (1982) Molecular Cloning: A Laboratory Manual, Cold Spring Harbor Laboratory, Cold Spring Harbor, N.Y., and the transformation protocol using Rb++/Ca++ treated cells was essentially according to this reference. Transformed cells were plated on four 8 cm diameter Petri dishes containing Luria broth agar and 100 micrograms/ml ampicillin and then incubated for 16 hours at 37° C. to allow for the growth of ampicillin resistant transformants into small colonies. Colonies were screened for the presence of the appropriately sized plasmid using the "colony crack" method (Maniatis et al., 1982, id.). The resulting plasmid was checked for appropriate restriction sites and for promoter activity for both polymerases to verify the construction shown in FIG. 1. The plasmid pGEM-1 has the promoter and multiple cloning site sequence shown in FIG. 6. This vector within *E. coli* HB101 has been deposited in the Agricultural Research Culture Collection, Peoria, Ill., U.S.A. under accession number NRRL B 15942.

EXAMPLE 2

Construction of plasmid pGEM-2

Figure 5:
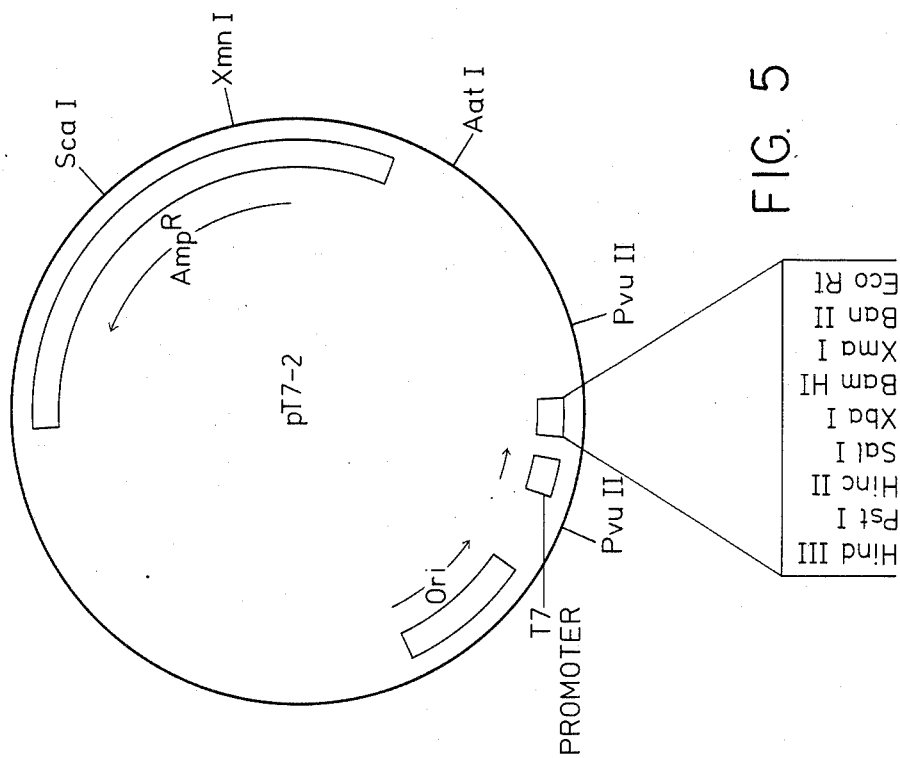
FIG. 5 is a partial restriction site and functional map of the parent plasmid pT7-2.
Figure 7:
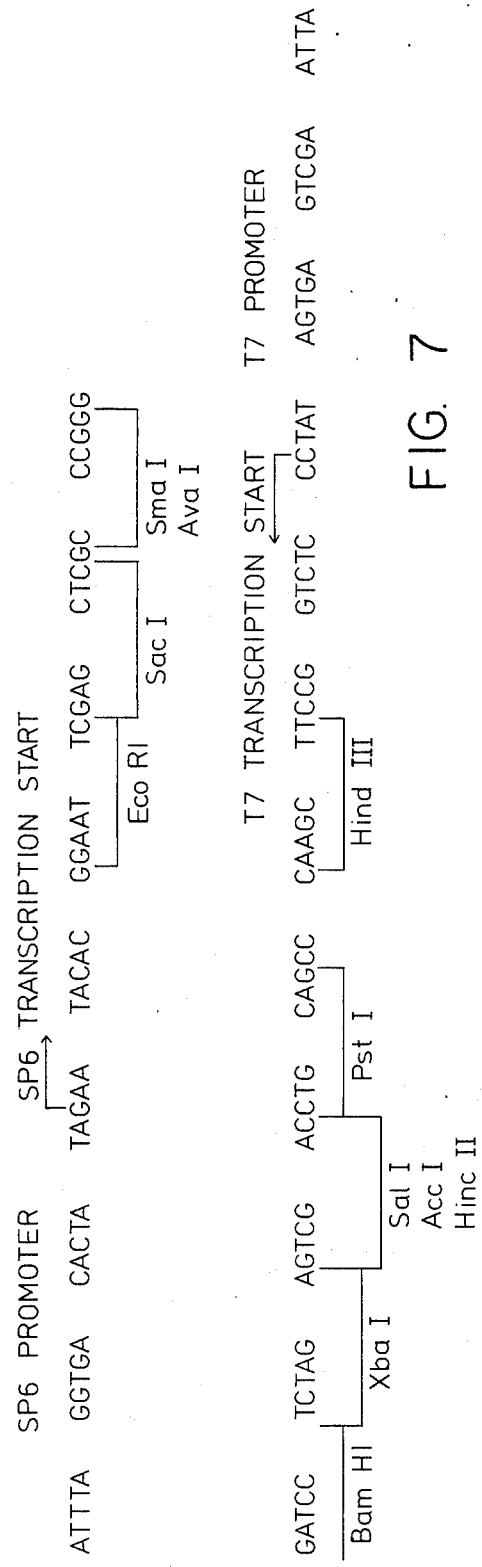
FIG. 7 is the promoter and multiple cloning site sequence for the plasmid pGEM-2 showing the coding strand for T7 RNA polymerase and the non-coding strand for SP6 RNA polymerase.

The construction of another plasmid, designated pGEM-2, followed the same procedures as in Example 1 except that the parent plasmids were pSP65 (Krieg and Melton, Nucleic Acids Res. 1984, id.) and pT7-2 (Tabor and Richardson, 1985, id.). pT7-2 has the partial restriction and functional map shown in FIG. 5 and is available from United States Biochemicals, Cleveland, Ohio. The plasmids were cut with the restriction enzymes Hind III and Pvu II and religated to insert the T7 promoter in the same manner as that described in Example 1. A partial restriction and functional map of the resulting plasmid pGEM-2 is shown in FIG. 2 and this plasmid has the promoter and multiple cloning site sequence shown in FIG. 7. This vector within *E. coli* HB101 has been deposited in the Agricultural Research Culture Collection, Peoria, Ill., U.S.A. under accession number NRRL B 15943.

EXAMPLE 3

Construction of plasmid pGEM-0 and Insertion of foreign DNA into the plasmid and purification of the template Cloning of DNA into a pGEM-type plasmid (i.e., a plasmid having opposed promoters separated by a multiple cloning site) and purification of the plasmid for use as a template is accomplished by standard cloning techniques. The pGEM plasmid is digested with one or (if a directional cloning strategy is to be employed) two different restriction endonucleases, and mixed together with a foreign DNA fragment having ends corresponding to those generated by digestion of the pGEM vector. Generally, the restriction enzyme(s) chosen will have a single recognition and cleavage site lying within the multiple cloning site of the vector and will recognize and cleave no other site on the vector. Following ligation with DNA ligase, the mixture is used to transform competent bacteria to ampicillin resistance as described in Example 1. pGEM vectors containing inserts of foreign DNA are distinguished from the parent plasmids based on their size as estimated by electrophoresis in agarose gels and staining with ethidium bromide following "colony cracks" to release the plasmid DNA from transformants (Maniatis et al., supra 1984). A specific example follows.

Figure 3:
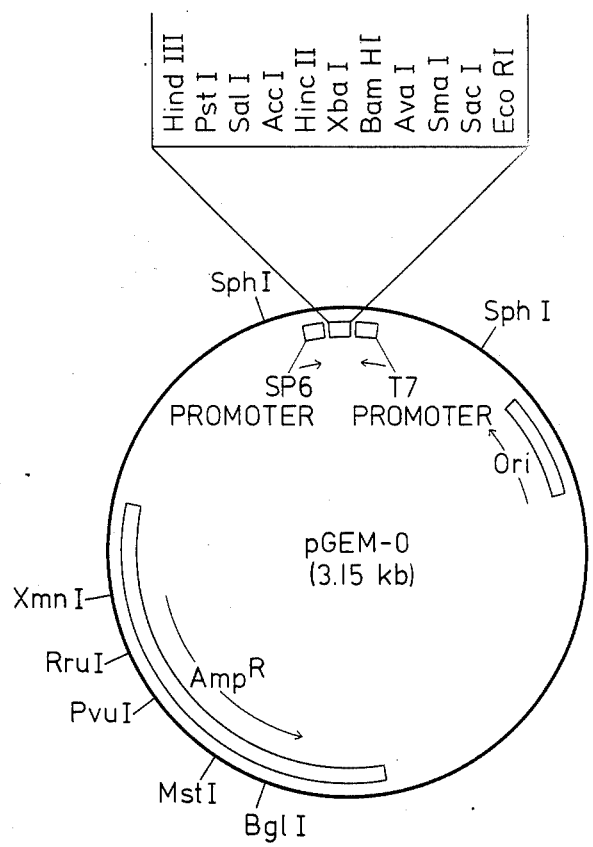
FIG. 3 is a partial restriction site and functional map of the plasmid pGEM-0.

A plasmid designated pGEM-0 having the partial restriction and functional map shown in FIG. 3 and the promoter and cloning site sequence shown in FIG. 8 was constructed from the parent plasmid pSP64 (Krieg and Melton, supra 1984) which supplies the pUC-12 DNA replication origin, ampicillin resistance gene, M13 multiple cloning site (MCS) and the SP6 promoter, and the parent plasmid pAR2192 (Studier, supra, 1984) which supplies the T7 promoter. To construct the pGEM-0 plasmid, the Bam H1 site in pAR2192 was removed by cutting with Bam H1, filling the ends with the Klenow fragment of DNA Polymerase I, and rejoining by blunt-end ligation. Specifically, one microgram of pAR2192 was digested for 1 hour at 37° C. with 16 units of Bam H1 (Promega Biotec, Madison, Wis.) in a volume of 0.05 ml in buffer consisting of 20 mM Tris-HCl, pH 7.4, 7 mM MgCl$_2$, 100 mM NaCl, 2 mM 2-mercaptoethanol and 0.1 mg/ml BSA. Following incubation, 0.5 microliters of 10% diethylpyrocarbonate (DEPC) (in ethanol) was added and the reaction then incubated for 10 minutes at 65° C. The reaction was then cooled to 20° C. and 2 microliters of 10× deoxyribonucleotide mix and 1 microliter of Klenow fragment (13 units/microliter, Promega Biotec, Madison, Wis.) was added (10× deoxyribo-nucleotide mix=4 mM each dATP, dGTP, dTTP and dCTP). Following a 15 minute, 20° C. incubation, 0.5 microliters of 10% DEPC was added and the reaction heated at 65° C. for 10 minutes. The reaction was then cooled to 25° C., 3 microliters of 10× ligase buffer and 20 units of T4 DNA ligase were added and the reaction was incubated for 16 hours at 25° C. The reaction was then heated for 10 minutes at 65° C. to inactivate the ligase and 1 microliter of 16 units/microliter Bam H1 was added and the reaction incubated for 30 minutes at 37° C. 5 microliters of the reaction was then used to transform 0.2 ml of competent *E. coli* HB101. Transformed cells were plated on plates containing Luria broth agar and 100 micrograms/ml ampicillin and incubated 16 hours at 37° C. Four of the resulting colonies were used to innoculate 50 ml Luria broth cultures (containing 100 micrograms/ml ampicillin) and the cultures grown at 37° C. for 16 hours. Plasmid DNA was then isolated from these cultures by procedures described below. Each of the plasmid DNAs was tested for the absence of the Bam H1 site by digestion with Bam H1 as described above and electrophoresis on gels containing 1% agarose and 1 microgram/ml ethidium bromide. Each of the four was found to be resistant to cutting by Bam H1. Digestion of the Bam H1 deleted plasmid with Eco R1 and Hinc II yields one large and two small (0.325 and 0.45 kb) fragments. The T7 RNA polymerase promoter is on the 0.325 kb fragment. This fragment was cloned into pSP64 by digesting Bam H1 deleted pAR2192 with Eco R1 and Hinc II, digesting pSP64 with Eco R1 and Pvu II, mixing the digests together and ligating. 0.5 micrograms pSP64 was digested with 20 units Eco R1 (Promega Biotec, Madison, Wis.), and 12 units Pvu II (Promega Biotec, Madison, Wis.) in a volume of 25 microliters containing 90 mM Tris-HCl, pH 7.5 50 mM NaCl, 10 mM $MgCl_2$ and 0.1 mg/ml BSA for 1 hour at 37° C. One microgram Bam H1 deleted pAR2192 was digested with 20 units Eco R1 and 18 units Hinc II in a volume of 25 microliters for 1 hour at 37° C. in the same buffer. Following the addition of 0.5 microliters 10% DEPC to each and heating at 65° C. for 10 minutes, the reactions were mixed together and 5 microliters of 10× ligase buffer and 20 units T4 DNA ligase added. Incubation was then allowed to proceed for 16 hours at 22° C. 24 units of Pvu II was then added and the reaction incubated for 30 minutes at 30° C. 0.010 ml was used to transform 0.2 ml of competent *E. coli* HB101. The desired pGEM-0 construction shown in FIG. 3 was selected by plasmid size screening on agarose gels following "colony cracks" and in vitro transcription with both T7 and SP6 RNA polymerases to demonstrate the presence of both promoters on the plasmid. The pGEM-1 and pGEM-2 plasmids differ from pGEM-0 by having fewer bases between the T7 promoter and the multiple cloning site (MCS).

Figure 9:
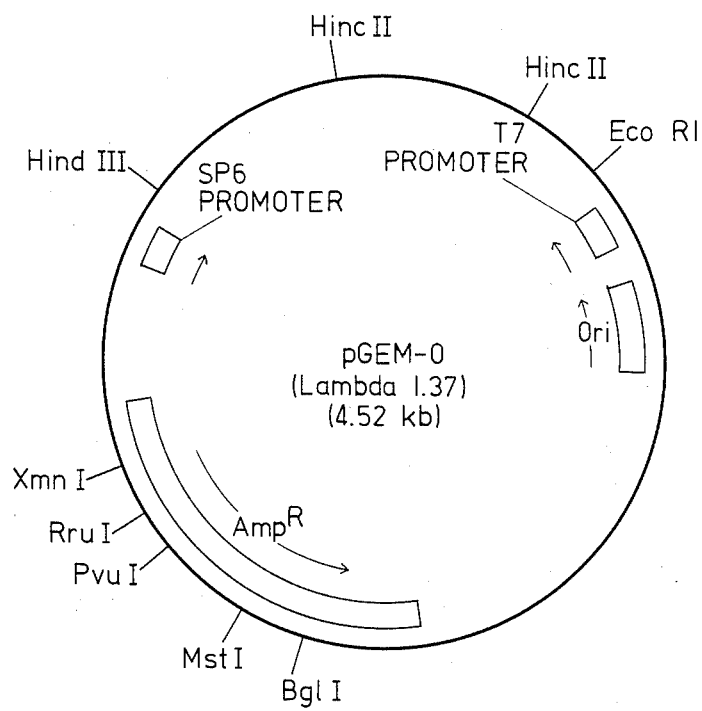
FIG. 9 is a partial restriction and functional map for the cloned plasmid pGEM-0 (lambda 1.37).

A 1.37 kb Eco R1-Hind III lambda phage DNA fragment is commercially available in a control plasmid ("RIBOPROBE" control plasmid, Promega Biotec, Wisconsin, Wis.). This fragment was excised from the control plasmid and inserted into the pGEM-0 vector in the following manner. One microgram control plasmid was digested with 20 units Eco R1 and 18 units Hind III in a volume of 50 microliters containing 10 mM Tris-HCl, pH 7.5, 7 mM $MgCl_2$, 60 mM NaCl and 0.1 mg/ml BSA for 1 hour at 37° C. One microgram of pGEM-0 was digested with the same enzymes under the same conditions. To each was then added 0.50 microliters 10% DEPC and the reactions heated for 10 minutes at 65° C. The reactions were then cooled to 22° C., mixed together, and following addition of 10 microliters 10× ligase buffer and 20 units T4 DNA ligase, were incubated for 2 hours at 22° C. The reaction was then heated for 10 minutes at 65° C. and 10 microliters were used to transform 0.2 ml competent *E. coli* HB101 to ampicillin resistance. Transformants were lysed and plasmid size estimated by electrophoresis on an agarose gel and staining with ethidium bromide. A 4.5 kb plasmid was identified in several of the lysates, corresponding to the size expected for the insertion of the 1.37 kb lambda DNA fragment from the control template into the pGEM-0 vector. The correct construction was confirmed by restriction endonuclease mapping and by transcription with both SP6 and T7 RNA polymerases. This cloned vector is referred to as PGEM-0 (lambda 1.37) vector and has the partial restriction and functional map shown in FIG. 9.

PURIFICATION OF RECOMBINANT PLASMIDS

Recombinant plasmids can be purified from large-scale bacterial cultures using standard procedures involving equilibrium density gradient centrifugation in cesium chloride gradients containing ethidium bromide (Maniatis et al., supra 1984) or by procedures not employing ultracentrifugation. These latter procedures involve cell lysis in alkaline sodium dodecyl sulfate, precipitation of the bulk of contaminating RNA with ammonium acetate, selective precipitation of plasmid DNA with polyethylene glycol, chloroform and phenol extraction to remove protein, and concentration of plasmid DNA by ethanol precipitation.

The pGEM type cloning vectors and recombinant plasmids derived from them by cloning procedures must be purified from bacterial extracts to enable them to be suitable for transcription in vitro. Minimally, the DNA preparations must be free from deoxyribonuclease, ribonuclease and nucleoside triphosphatase activities as well as free from inhibitors of RNA polymerase activity. The following procedure yields a highly purified and intact plasmid DNA product that is suitable not only for in vitro transcription reactions but also for other types of manipulations performed on DNA in the molecular biology laboratory. The product is free from the above mentioned contaminants as well as chromosomal DNA and low molecular weight nucleic acid contaminants. Other standard, published methods of purifying plasmid DNA may be substituted for this method provided that the DNA template is checked for its suitability in transcription reactions as discussed above. See, e.g., Maniatis, T., Fritsch, E. F., and Sambrook, J., *Molecular Cloning--A Laboratory Manual*, 1982, Cold Spring Harbor Laboratory.

Pure bacterial cultures for plasmid DNA purification are grown to saturation, without amplification with chloramphenol, in desired volumes of culture media such as L broth and in the presence of the antibiotic ampicillin at a concentration of 100 ug/ml. Many compatible bacterial hosts such as *E. coli* HB101 (ATCC #33694), C600, etc. can be used to propagate the plasmid DNA in culture. Cells are harvested by centrifugation and can be used immediately (fresh cells) or bacterial pellets can be stored frozen at −70° C. for at least one year with no apparent changes in yield or purity of the plasmid DNA product. The following steps are carried out:

(1) Thoroughly resuspend cells (fresh or frozen) in 10 volumes of room temperature 25 mM Tris-HCl, 50 mM EDTA (pH 8.0) in an Erlenmeyer flask of suitable size. (For 50 g of cells, a 4 liter flask is appropriate). (2) Add 2 volumes (based on the volume of buffer used in Step 1) of room temperature 0.20M NaOH, 1% SDS (freshly prepared), and mix thoroughly by vigorous swirling. Place on ice for 10 minutes. (3) Add 1.5 volumes (based on the volume of buffer used in Step 1) of ice-cold 5M potassium acetate pH 4.8.Mix thoroughly by vigorous swirling of the flask. Place on ice for 5 minutes. A heavy, flocculent precipitate will be seen. (4) Centrifuge the mixture for 15 minutes at 9000 g (4° C.). Decant the supernatant solution to a fresh flask through a Miracloth filter (Sigma Chemical Company, St. Louis, Mo.). (5) Add 0.6 volumes of 2-propanol (based on the volume of the supernatant solutions in Step 4). Mix well. Let sit at room temperature for 1 hour. (6) Centrifuge as in Step 4. Discard the supernatant solution. (7) Dissolve the precipitate in room temperature 10 mM Tris-HCl, 1 mM EDTA (pH 8.0), which will be herein referred to as TE buffer. (For 50 g of starting material, this can be done in 100 ml of buffer.) (8) Add 1 volume of room temperature 5M ammonium acetate solution (neutral pH, 7) to the solution from Step 7. (A heavy precipitate forms.) Place on ice for 20–30 min. (This mixture can be stored overnight in the refrigerator if time constraints arise). (9) Centrifuge as in Step 4. Save the supernatant solution and discard the pellet. (10) Add 2 volumes of 95% or absolute ethanol (room temperature or ice cold) to the supernatant solution from Step 9. Mix well and place on ice for 20–30 minutes. Centrifuge as in Step 4. Discard the supernatant solution. (11) Dissolve the pellet in a suitable volume of room temperature TE buffer (see Step 7 above). For 50 g of starting material, use minimally 5 ml of buffer. The solution should be as concentrated as possible but not have detectable viscosity. Increase the volume as needed with TE buffer. Add preheated (80° C. for 10 minutes, to destroy any trace DNase activity) RNase A to a final concentration of 10 ug/ml. Incubate at 37° C. for 15 minutes. (12) Add 5M NaCl (room temperature) to a final concentration of 1.5M to the solution. (13) Add ¼ volume of room temperature 30% PEG 6000 or 8000 containing 1.5M NaCl and mix well. Incubate on ice for 30 minutes. (This solution may also be stored overnight at 0° C. if time constraints are present). (14) Centrifuge as in Step 4 (7500 rpm if using 30 ml Corex centrifuge tubes) at 4° C. Discard the supernatant solution. (15) Dissolve the precipitate by swirling in room temperature TE buffer. See Step 11 above for guidelines to selection of the appropriate volume. This precipitate may require over 30 minutes to dissolve completely. Extract the solution with 1 volume of chloroform/isoamyl alcohol (24:1) (Maniatis et al., id.) in Corex centrifuge tubes. Centrifuge at 7500 rpm for 15 minutes at room temperature. Collect the aqueous phase with a Pasteur pipette. (16) Add 5M NaCl to 0.5M and extract the solution with 1 volume of phenol/chloroform (1:1) saturated with TE buffer and 0.5M NaCl. Centrifuge as in Step 15 and collect the supernatant solution. (17) Precipitate the DNA from the solution by adding 2 volumes of ethanol. After mixing well, place on ice for 15 minutes. Centrifuge as in Step 15 and discard the supernatant solution. (18) Dissolve the precipitate in a small volume of water (See guidelines in Step 7 above for an appropriate volume.) Chill the solution on ice. Adjust to 0.075M NaCl (from a 5M stock solution) and 0.05M sodium acetate, pH 4.0 (from a 2M stock solution). (19) Extract the solution with 0.05M sodium acetate pH 4.0-buffered phenol by vortexing the mixture occasionally over a 5 minute period. Be certain to keep the solution as cold as possible (0° C.). Centrifuge at 7500 g at 4° C. Collect the aqueous (top) phase. (20) Precipitate the DNA with ethanol (see Step 17). Dissolve the pellet in a suitable volume (see guidelines in Step 7 above) of TE buffer containing a 0.1M NaCl. (21) Precipitate the DNA with ethanol again and collect by centrifugation. Discard the supernatant solution and drain the centrifuge tubes on absorbant paper. Dry the precipitates under vacuum and dissolve in a suitable volume of TE buffer.

The concentration and purity of the purified plasmid DNA may be determined by standard analytical spectrophotometric methods. The DNA solution can be stored at 0°–4° C. for short term needs. If desired, the solution can also be stored in aliquots at −70° C. if long-term storage is necessary.

EXAMPLE 4

In Vitro Production of RNA

Production of RNA from the template described in Example 3 may be accomplished by established procedures. Typically, recombinant plasmid DNA to be transcribed is first linearized by digestion with a restriction endonuclease which cuts at the 3' (promoter distal) terminus of the insert. In this manner, only the insert sequences and not the vector sequences are transcribed. Note that the designation "promoter distal" refers to the promoter for that RNA polymerase (either SP6 or T7) which is to be used for transcription.

pGEM-0 (lambda 1.37) vector was linearized by digesting individually with Eco R1, Hind III and Hinc II and the digests mixed together in equimolar portions to form a control template. Specifically, 2.5 mg units of pGEM-0 (lambda 1.37) vector were digested with 1000 units Eco R1, Hind III, and Hinc II for 5 hours at 37° C. in volumes of 5 ml in the buffers recommended by the manufacturer. Reactions were monitored for completeness by electrophoresis on agarose gels and staining with ethidium bromide. Then to each reaction was added 0.05 ml 10% DEPC (in ethanol) and the reactions vortexed and then heated at 65° C. for 10 minutes. Each reaction was then extracted once with phenol:chloroform (1:1 in 50 mM Tris-HCl pH 7.9, 1 mM EDTA, 15 mM 2-mercaptoethanol, 0.5M NaCl, 0.1% 8-hydroxyquinoline), once with chloroform:isoamyl alcohol (24:1) and then precipitated twice with two volumes each time of 100% ethanol. The final ethanol pellets were vacuum-dried and dissolved in 1 ml 10 mM Tris-HCl pH 7.9, 0.1 mM EDTA. A 100 fold dilution of each digest was then scanned from 340 nm to 220 nm and the DNA concentration determined assuming a 1 mg/ml solution, giving an absorbance of 20 at 260 nm. Digestions were then diluted to 1 mg/ml with 10 mM Tris-HCl pH 7.9, 0.1 mM EDTA, and equal volumes of each of the three were mixed together to form the control template.

The control template was separately transcribed with SP6 and T7 RNA polymerases. Transcription reactions each contained (in a total volume of 20 microliters) an RNA generating medium composed of 40 mM Tris-HCl pH 7.9, 6 mM MgCl$_2$, 2 mM spermidine, 10 mM NaCl, 10 mM dithiothreitol, 0.5 mM each of ATP, CTP, GTP and UTP, 2.5 micro Curies of alpha-$^{32}$P-CTP, 1 microgram control template, and 7 units of SP6 or T7 RNA polymerase. The mixtures were incubated at 37° C. for 30 minutes, followed by the addition of 20 microliters of a solution of formamide containing 10% sucrose and tracking dyes. After heating at 65° C. for 5 minutes the reactions were quickly brought to room temperature and 10 microliter samples layered on a 5% polyacrylamide gel containing 7M urea. Following electrophoresis the gel was exposed to X-ray film to visualize labeled transcripts and additionally the transcripts were visualized by staining with ethidium bromide. Transcription with SP6 RNA polymerase generates run-off transcripts 11 bases, 172 bases and 1386 bases long while transcription with T7 RNA polymerase generates transcripts 43 bases, 679 bases and 1418 bases long.

It is understood that the invention is not limited to the particular embodiments specifically disclosed herein as exemplary, but embraces such modified forms thereof as come within the scope of the following claims.

What is claimed is:

1. A method of producing RNA copies in vitro of a selected DNA sequence, comprising the steps of:
   (a) providing a DNA cloning vector comprised of double stranded DNA having two different phage promoter sequences facing each other such that transcription from either phage promoter proceeds in the opposite direction of transcription from and toward the other phage promoter, each phage promoter sequence recognized by a phage encoded RNA polymerase which is specific to that phage promoter and which recognizes no other sequence in the vector, the two phage promoters having located between them a cloning site composed of a sequence of DNA base pairs which includes at least one restriction endonuclease cleavage site which is cleaved by an endonuclease which cleaves no other site on the vector;
   (b) applying to the vector a restriction enzyme specific to a selected restriction site between the two opposed phage promoters to cleave the vector at said site;
   (c) inserting the selected DNA sequence into the cleaved site;
   (d) cloning the vector with the inserted DNA sequence in a suitable host;
   (e) purifying the vector with the inserted DNA sequence and resuspending said vector in an aqueous solution;
   (f) applying a restriction enzyme to the vector which recognizes a restriction site between the inserted DNA and one of the opposed phase promoters to cleave the vector at said site; and
   (g) applying to the cleaved vector the phage encoded RNA. polymerase specific to the phase promoter remaining adjacent to the inserted DNA segment in an RNA generating medium to provide RNA copies of the selected DNA sequence.

2. The method of claim 1 wherein the selected DNA sequence is inserted into a plurality of copies of the vector and, after the step of cloning the vector with the inserted DNA sequence and before the step of applying a restriction enzyme, further comprising the step of dividing the aqueous solution containing the vectors carrying the inserted DNA sequence into two groups, in step (f) cleaving one group with a restriction enzyme specific to a site between the inserted DNA sequence and the first one of the two phage promoters and cleaving the second group with a restriction enzyme specific to a site between the inserted DNA sequence and the second of the two phage promoters, and in step (g) applying the two phage encoded RNA polymerases which are specific to the two phase promoter sequences in an RNA generating medium whereby both strands of the inserted DNA sequence will be transcribed and the RNA transcribed from the opposite strands will be available to hybridize to form double-stranded RNA.

3. The method of claim 1 wherein the vector provided is the plasmid pGEM-1.

4. The method of claim 1 wherein the vector provided is the plasmid pGEM-2.

5. The method of claim 1 wherein the two opposed promoter sequences in the vector provided are the SP6 and T7 late phage promoter sequences.

6. The method of claim 1 wherein the cloning site between the two opposed phage promoters on the vector provided has plural distinct restriction sites selected from the group consisting of sites cleaved by at least one of the following endonucleases; Hind III, PST I, Sal I, ACC I, Hinc II, Xba I, Bam HI, Ava I, Sma I, Sac I and Eco RI, and wherein the restriction enzyme or enzymes applied in step (b) is an endonuclease selected from the group consisting of at least one of Hind III, Pst I, Sal I, Acc I, Hinc II, Xba I, Bam HI, Ava I, Sma I, Sac I, and Eco RI which cleaves its restriction site to leave ends complementary to the ends of the selected DNA sequence.

7. A DNA cloning vector for use in production in vitro of RNA copies of a cloned DNA sequence comprising:
   double stranded DNA having two different phage promoter sequences facing each other such that transcription from either phage promoter proceeds toward the other phage promoter and in a direction opposite from the direction of transcription of the other phage promoter, each phage promoter sequence being one that is recognized by a phase encoded RNA polymerase which is specific to that phage promoter and which does not recognize the other phage promoter, the two phage promoters being located closely adjacent opposite sides of a cloning site composed of a sequence of DNA base pairs which includes at least one restriction enzyme cleavage site.

8. The vector of claim 7 wherein the two opposed promoters are the SP6 and T7 late phage promoter sequences.

9. The vector of claim 7 wherein the cloning site between the two opposed promoter sequences includes at least three restriction sites which are cleaved by three different restriction enzymes.

10. The vector of claim 7 wherein the cloning site between the two opposed promoters has plural distinct restriction sites selected from the group of sites cleaved by at least one of the following endonucleases; Hind III, Pst I, Sal I, Acc I, Hinc II, Xba I, Bam HI, Ava I, Sma I, Sac I, and Eco RI.

11. The vector of claim 10 wherein the two opposed promoters are the SP6 and T7 late phage promoter sequences.

12. A plasmid suited for in vitro production of RNA copies of a cloned DNA sequence comprising:
   an essentially pure plasmid in circular form having two different phage promoter sequences facing each other such that transcription from either phage promoter proceeds toward the other phage promoter and in a direction opposite from the direction of transcription of the other phage promoter, each phage promoter sequence being one that is recognized by a phase encoded RNA polymerase which is specific to that phage promoter and which does not recognize the other phage promoter, the two phage promoters being located closely adjacent opposite sides of a cloning site composed of a sequence of DNA base pairs which includes at least one restriction enzyme cleavage site.

13. The plasmid of claim 12 wherein the two opposed promoters are the SP6 and T7 late phage promoter sequences.

14. The plasmid of claim 12 wherein the cloning site between the two opposed promoter sequences includes at least three restriction sites which are cleaved by three different restriction enzymes.

15. The plasmid of claim 12 wherein the cloning site between the two opposed phage promoters has plural distinct restriction sites selected from the group of sites cleaved by at least one of the following endonucleases: Hind III, Pst I, sal I, Acc I, Hinc II, Xba I, Bam HI, Ava I, Sma I, Sac I, and Eco RI.

16. The plasmid of claim 15 wherein the two opposed promoters are the SP6 and T7 late phage promoter sequences.

17. The plasmid of claim 12 including a gene in the plasmid providing ampicillin resistance to competent *E. coli* bacteria when transformed by the plasmid.

18. The plasmid of claim 12 wherein the plasmid contains approximately 2.9 kilobases.

19. The plasmid of claim 12 which is pGEM-1.

20. The plasmid of claim 12 which is pGEM-2.

* * * * *